United States Patent
Bowen

Patent Number: 6,036,004
Date of Patent: Mar. 14, 2000

[54] MULTI-COMPARTMENT BAG WITH BREAKABLE WALLS

[76] Inventor: Michael L. Bowen, 7218 Royal Gate Dr., Arlington, Tarrant County, Tex. 76106

[21] Appl. No.: 08/984,372

[22] Filed: Dec. 3, 1997

[51] Int. Cl.⁷ .................................................. B65D 25/08
[52] U.S. Cl. ..................................... 206/219; 215/DIG. 8
[58] Field of Search ................................... 206/469, 219, 206/222; 383/38; 215/DIG. 8

[56] References Cited

U.S. PATENT DOCUMENTS

| | | |
|---|---|---|
| D. 327,329 | 6/1992 | Hubbard et al. . |
| 2,589,577 | 3/1952 | Rosenthal . |
| 2,898,744 | 8/1959 | Robbins . |
| 2,991,000 | 7/1961 | Spees . |
| 3,095,291 | 6/1963 | Robbins . |
| 3,149,943 | 9/1964 | Amador . |
| 3,173,602 | 3/1965 | Clipner . |
| 3,182,728 | 5/1965 | Zabriskie . |
| 3,186,628 | 6/1965 | Rohde . |
| 3,189,174 | 6/1965 | Cormack . |
| 3,191,392 | 6/1965 | Donnelly . |
| 3,294,227 | 12/1966 | Schneider et al. . |
| 3,298,597 | 1/1967 | Bellamy, Jr. . |
| 3,429,315 | 2/1969 | McDonald . |
| 3,491,761 | 1/1970 | Baker . |
| 3,542,032 | 11/1970 | Spencer, Jr. . |
| 3,608,709 | 9/1971 | Pike . |
| 3,627,611 | 12/1971 | Bonk . |
| 3,736,769 | 6/1973 | Petersen . |
| 3,744,625 | 7/1973 | Chin . |
| 3,749,620 | 7/1973 | Montgomery . |
| 3,756,389 | 9/1973 | Firth . |
| 3,763,622 | 10/1973 | Stanely, Jr. . |
| 3,785,111 | 1/1974 | Pike . |
| 3,807,118 | 4/1974 | Pike . |
| 3,847,279 | 11/1974 | Montgomery . |
| 3,865,117 | 2/1975 | Perry, III . |
| 3,874,504 | 4/1975 | Verakas . |
| 3,891,138 | 6/1975 | Glas . |
| 3,893,834 | 7/1975 | Armstrong . |
| 3,950,158 | 4/1976 | Gossett . |
| 3,983,994 | 10/1976 | Wyslotsky . |
| 4,000,996 | 1/1977 | Jordan . |
| 4,033,354 | 7/1977 | De Rosa . |
| 4,044,773 | 8/1977 | Baldwin . |

(List continued on next page.)

FOREIGN PATENT DOCUMENTS

| | | |
|---|---|---|
| 1263581 | 12/1989 | Canada . |
| 474249 | 10/1937 | United Kingdom . |

OTHER PUBLICATIONS

Zee Ice Pack Manufactured by Zee Service, Inc. of Irvine, California.

Spenco Portable Cold Pack Manufactured by Spenco Medical Corp of the United Kingdom.

U.S. Application No. 08/545,348 Filed Oct. 17, 1995, Entitled "Multi–Compartment Bag With Breakable Walls", Abandoned.

U.S. Application No. 08/954,844 Filed Oct. 21, 1997, Entitled "Multi–Compartment Bag with Breakable Waslls", Pending.

U.S. Application No. 08/559,469 Filed Nov. 15, 1995, Entitled "Hot Or Cold Chemical Therapy Pack", Allowed.

Primary Examiner—Paul T. Sewell
Assistant Examiner—Nhan T. Lam
Attorney, Agent, or Firm—Dority & Manning, P.A.

[57] ABSTRACT

The invention relates to a multi-compartment bag which provides for the separation of two substances until their desired intermixing. A specific application of this multi-compartment bag is for hot or cold chemical packs. The substances in the multi-compartment bag are separated by two breakable walls and a third compartment which together act as a barrier to migration of one substance into the second substance, which would reduce the shelf life and efficiency of the hot or cold chemical pack. The present invention's use of two breakable walls and a compartment, empty or containing an inert substance, separating two reactive substances, provides a longer shelf life, a high efficiency, more reliability and improved ease of operation.

16 Claims, 7 Drawing Sheets

U.S. PATENT DOCUMENTS

| | | |
|---|---|---|
| 4,057,047 | 11/1977 | Gossett . |
| 4,077,390 | 3/1978 | Stanely et al. . |
| 4,081,150 | 3/1978 | Tyson . |
| 4,081,256 | 3/1978 | Donnelly . |
| 4,204,543 | 5/1980 | Henderson . |
| 4,226,330 | 10/1980 | Butler . |
| 4,227,614 | 10/1980 | Hollander, Jr. . |
| 4,239,105 | 12/1980 | Gilbert . |
| 4,276,263 | 6/1981 | Andersen et al. . |
| 4,312,473 | 1/1982 | Hoeller . |
| 4,326,533 | 4/1982 | Henderson . |
| 4,347,848 | 9/1982 | Hubbard et al. . |
| 4,372,318 | 2/1983 | Viesturs et al. . |
| 4,385,950 | 5/1983 | Hubbard et al. . |
| 4,397,315 | 8/1983 | Patel . |
| 4,402,402 | 9/1983 | Pike . |
| 4,427,010 | 1/1984 | Marx . |
| 4,458,811 | 7/1984 | Wilkinson . |
| 4,462,224 | 7/1984 | Duncshee et al. . |
| 4,465,488 | 8/1984 | Richmond et al. . |
| 4,496,046 | 1/1985 | Stone et al. . |
| 4,519,499 | 5/1985 | Stone et al. ............................ 206/219 |
| 4,523,353 | 6/1985 | Hubbard et al. . |
| 4,527,566 | 7/1985 | Abare . |
| 4,537,184 | 8/1985 | Williams, Jr. . |
| 4,585,003 | 4/1986 | Meistrell . |
| 4,586,506 | 5/1986 | Nangle . |
| 4,628,932 | 12/1986 | Tampa . |
| 4,636,391 | 1/1987 | Pike . |
| 4,668,564 | 5/1987 | Orchard . |
| 4,688,572 | 8/1987 | Hubbard et al. . |
| 4,751,119 | 6/1988 | Yukawa . |
| 4,770,295 | 9/1988 | Carveth et al. . |
| 4,780,117 | 10/1988 | Lahey et al. . |
| 4,805,620 | 2/1989 | Meistrell . |
| 4,823,985 | 4/1989 | Grollier et al. . |
| 4,854,760 | 8/1989 | Pike et al. . |
| 4,856,651 | 8/1989 | Francis . |
| 4,931,333 | 6/1990 | Henry . |
| 4,951,666 | 8/1990 | Inman et al. . |
| 4,953,550 | 9/1990 | Dunshee . |
| 4,972,832 | 11/1990 | Trapini . |
| 4,986,076 | 1/1991 | Kirk et al. . |
| 5,020,711 | 6/1991 | Kelley . |
| 5,045,041 | 9/1991 | Murphy . |
| 5,074,300 | 12/1991 | Murphy . |
| 5,109,841 | 5/1992 | Hubbard et al. . |
| 5,163,504 | 11/1992 | Resnick . |
| 5,178,139 | 1/1993 | Angelillo et al. . |
| 5,184,470 | 2/1993 | Moser et al. . |
| 5,205,278 | 4/1993 | Wang . |
| 5,261,241 | 11/1993 | Kitahara et al. . |
| 5,267,646 | 12/1993 | Inoue et al. . |
| 5,275,156 | 1/1994 | Milligan et al. . |
| 5,353,927 | 10/1994 | Stupar et al. . |
| 5,356,426 | 10/1994 | Delk . |
| 5,466,251 | 11/1995 | Brunson et al. . |
| 5,492,219 | 2/1996 | Stupar ..................................... 206/219 |
| 5,545,197 | 8/1996 | Bowen . |
| 5,641,325 | 6/1997 | Delk et al. . |
| 5,723,002 | 3/1998 | Delk et al. . |

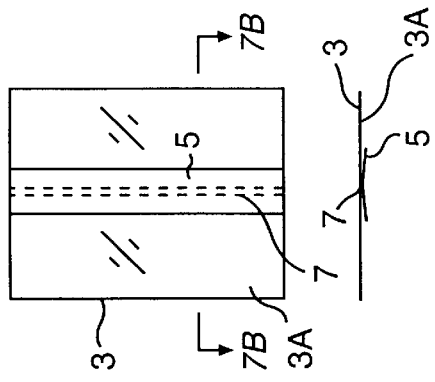
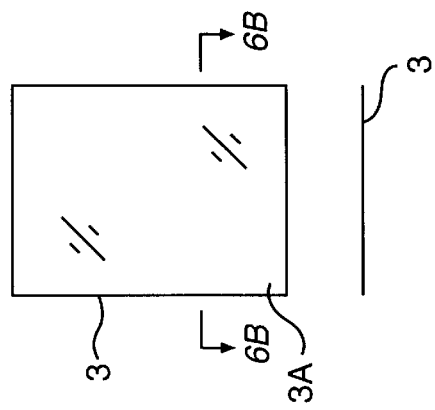
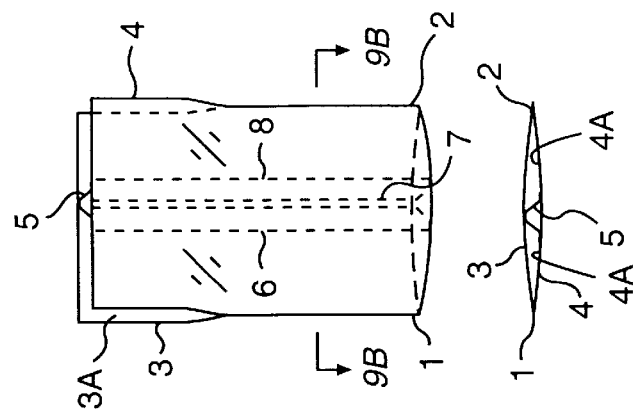
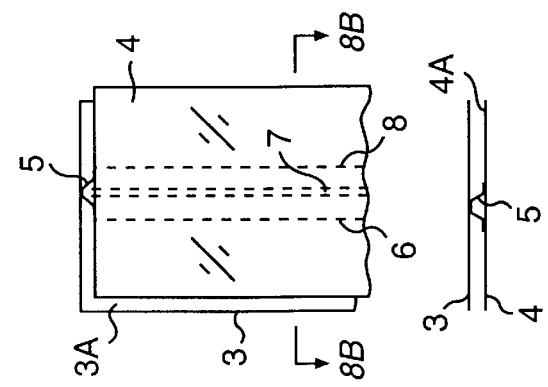
FIG. 6A
FIG. 6B
FIG. 7A
FIG. 7B
FIG. 8A
FIG. 8B
FIG. 9A
FIG. 9B

MULTI-COMPARTMENT BAG WITH BREAKABLE WALLS

RELATED APPLICATIONS

This application is related by subject matter to copending, co-owned U.S. application Ser. No. 08/403,295, filed Mar. 14, 1995, "A Reusable Hot or Cold Chemical Therapy Pack", and copending application Ser. No. 08/954,844.

TECHNICAL FIELD OF THE INVENTION

This invention relates to a multi-compartment bag for mixing a first substance with a second substance. More particularly, this multi-compartment bag utilizes first and second breakable walls with a compartment there-in-between which acts as a barrier to pre-activation intermixing of the first substance and the second substance. A desired use of the multi-compartment bag is hot or cold chemical packs.

BACKGROUND OF THE INVENTION

Multi-compartment bags are known for use in a variety of applications, including mixing two reactants to produce an endothermic or exothermic reaction for a number of uses, including therapy for muscular injury or circulatory problems or heating or cooling food. Multi-compartment bags have also been used for applications such as mixing resins with an initiator prior to use of the resin.

Cold packs have been used to treat injuries such as sprained muscles or injured joints. Generally, the cold packs are used to slow blood flow, and reduce swelling, pain and further damage.

Heat packs have been used to warm muscles or reduce cramping. Generally, heat packs increase blood flow.

Hot and cold packs are generally of two types: those that require external heating or cooling, and "chemical packs" which mix two or more reactants to cause an endothermic or exothermic reaction. It is desired that chemical packs have a long shelf life and be activated only upon an intentional activation, and not in shipping or handling.

The chemical packs generally come in two varieties: the bag-in-bag type or the side-by-side type. The bag-in-bag type pack has two separate bags, with a smaller bag containing one of the reactants included within the larger bag which contains the other reactant. Bag-in-bag chemical packs suffer from the significant disadvantage that there is a large surface area, represented by the exterior surface of the smaller bag, between the first reactant and the second reactant. Here, if a reactant is a liquid or gas, it will migrate through the plastic material of the smaller bag and into the second reactant causing a pre-activation intermixing of the reactants which results in a short shelf life and a lower efficiency upon intentional activation. This migration through the smaller bag can be slowed by using a thicker plastic material for the smaller bag; however, when a thicker smaller bag is utilized, it becomes more difficult to activate the pack when activation is desired. Also, with the bag-in-bag design, it is sometimes difficult to rupture the smaller bag. A number of prior art devices have utilized a rigid spike to facilitate rupturing the smaller bag. This presents significant shortcomings in that the rigid spike may puncture the larger bag in use or in shipping and handling causing external leaking.

The side-by-side bags utilize a breakable seal between two compartments located side-by-side, each compartment containing one of the reactants. These side-by-side packs attempt to utilize a strong seal around the perimeter of the bag and a weak seal to separate the two compartments. This is very difficult to do on a consistent basis and with known manufacturing techniques and leads to a situation where a force, intended to mix the two reactants, breaks an exterior seal causing a leak of the reactants onto the potential user.

Various mechanical devices have been used to prevent the mixing of two components in multi-compartment bags. These mechanical devices may be either externally mounted or internal to the bag, such as, for example, a groove provided on the inner side of one sheet which connects with a rib on the inner side of the opposite sheet, the groove and rib being engaged to seal and prevent intermixing of the two reactants, with the rib and groove being separated to permit intermixing. These mechanical seals suffer from significant shortcomings. First, mechanical seals invariably leak and are not as reliable as other sealing methods. Also, during shipping and handling, mechanical seals have a higher rate of accidental activation, resulting in unusable product.

U.S. Pat. No. 4,427,010 to Marx utilizes a side-by-side bag wherein a breakable wall is used instead of a breakable seal. This overcomes the problem of manufacturing a seal which ruptures at the desired force; however, this bag still has the significant shortcoming of a large surface area between the first and second reactants which, upon migration of one reactant through the plastic sheet into the other reactant, reduces the shelf life and efficiency of the product.

Another shortcoming of the prior art chemical packs is that they do not provide any means to fasten the chemical pack to a user wishing to apply the chemical pack in a therapeutic fashion to a particular part of his body. Prior art ice packs, i.e., packs wherein ice is added for each use, have employed ties and other fastening means. However, these ice pack fastening means suffer from several shortcomings. First, if not used carefully or if overstressed, these fastening means may cause the rupturing of a seam or tearing of a pack resulting in external leaking of ice and water. While this is an undesired result with ice packs, it presents a much more serious concern with chemical packs, where the rupturing of a seal or tearing of a pack could result in release of chemicals onto the user. Also, depending upon the ice pack chosen, the ties may be difficult to use or expensive to manufacture.

There exists a need for a multi-compartment bag for mixing two substances, and more particularly, for a hot or cold chemical pack for mixing two substances, which has a long shelf life and wherein the force required to mix the two substances is predictable, such that the substances will be mixed upon an intended activation by the user, and not in normal handling and shipping. There further exists a need for a chemical pack with suitable ties for fastening the chemical pack to a user.

SUMMARY OF THE INVENTION

The invention relates to a multi-compartment bag for mixing a first substance with a second substance where the two substances are separated by a compartment which is empty or which holds an inert substance. The first compartment holding the first substance is separated from the third compartment, which is empty or which holds an inert substance, by a first breakable wall, and the second compartment holding the second substance is separated from the third compartment by a second breakable wall. The two breakable walls and the third compartment act as an effective barrier for migration of one substance into the other substance which would lead to a short shelf life or a low efficiency reaction upon intentional activation.

It is an object of this invention to provide a hot or cold chemical pack which has a long shelf life.

It is further an object of this invention to provide a hot or cold chemical pack which upon intentional activation is easily activated, but which is able to withstand shipping and handling without unintentional activation.

It is still further an object of this invention to provide a hot or cold chemical pack which has suitable ties to enhance its usefulness.

BRIEF DESCRIPTION OF THE DRAWINGS

For a more complete understanding of the present invention, and the advantages thereof, reference is now made to the following descriptions taken in conjunction with the accompanying drawings, in which:

FIGS. 6A, 6B, 7A, 7B, 8A, 8B, 9A, 9B, 10 show the method of manufacturing the multi-compartment bag of FIGS. 1 and 2.

DETAILED DESCRIPTION OF EXEMPLARY EMBODIMENTS

The preferred embodiments of the present invention and its advantages are best understood by reference to FIGS. 1–18 of the drawings, like numerals being used for like and corresponding parts of the various drawings.

Figure 1:
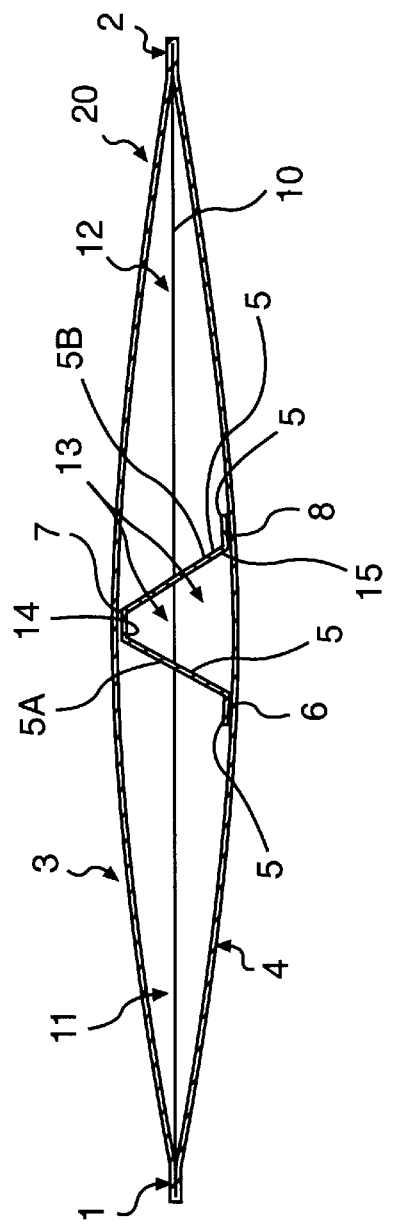
FIGS. 1 and 1A are side views of a multi-compartment bag with breakable walls designed for holding two substances.

FIG. 1 shows a multi-compartment bag 20 having a first compartment 11 and second compartment 12. The compartments 11 and 12 are separated by a first breakable wall 5A and a second breakable wall 5B. Breakable walls 5A and 5B serve as part of the perimeter of a third compartment 13 which separates the first compartment 11 and the second compartment 12 and which acts as a barrier to prevent migration of a substance contained in either compartment 11 or 12 into the other compartment 11 or 12.

Figure 2:
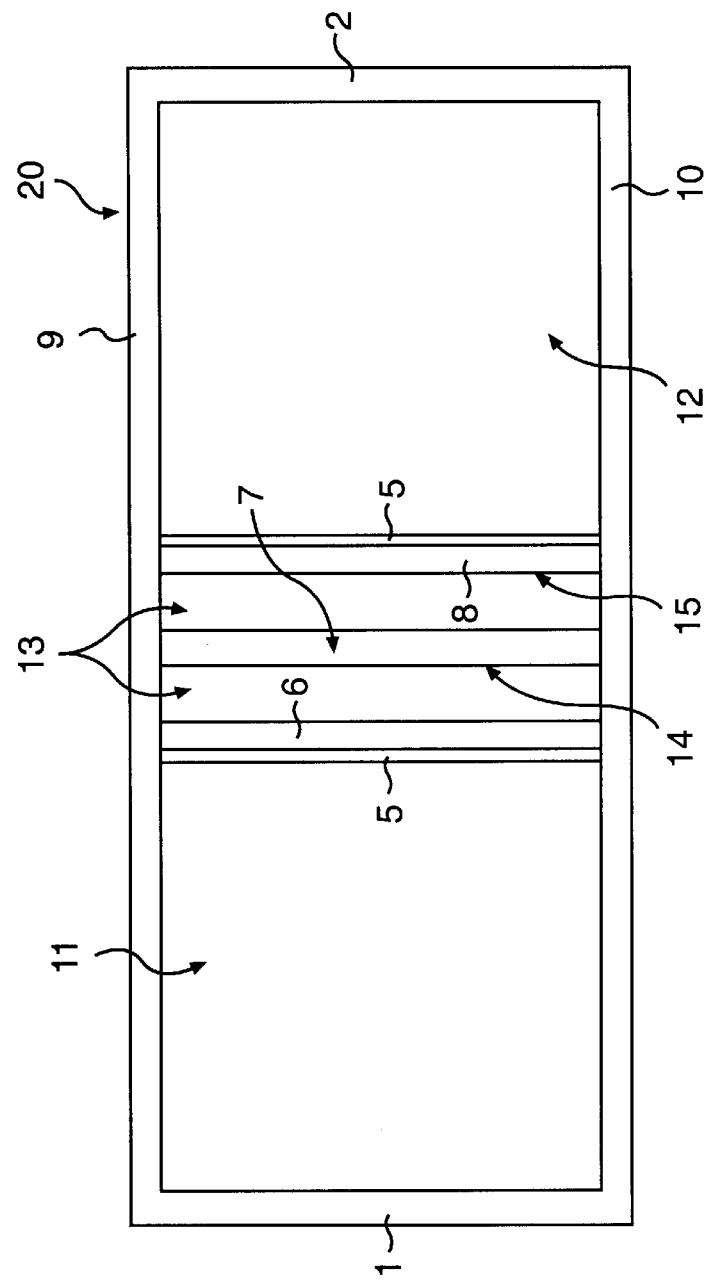
FIG. 2 is a top view of the FIG. 1 device.

FIGS. 1 and 2 show the overall construction of a three-compartment bag with two breakable walls 5A, 5B, which provides for the mixing of two substances. A first substance is stored in compartment 11 and a second substance is stored in compartment 12. This multi-compartment bag is constructed of a top sheet 3 and a bottom sheet 4 which is sealed on its ends via seals 1 and 2, and which is sealed about its perimeter by seals 1, 2, 9, and 10. This forms an internal compartment which is the combination of compartments 11, 12 and 13. Within this internal compartment is located breakable sheet 5 which separates the overall internal compartment into the three compartments 11, 12, and 13. Breakable sheet 5 is sealed to bottom sheet 4 via seal 6 which extends across the width of bottom sheet 4. The middle section of breakable sheet 5 is sealed to top sheet 3 at seal 7. Breakable sheet 5 is also sealed to the bottom sheet 4 at seal 8. Seals 7 and 8 extend across the width of the top sheet 3 and bottom sheet 4, respectively.

Thus, in the embodiment of FIGS. 1 and 2, there are formed three compartments 11, 12, 13. The first compartment 11 is formed by a perimeter consisting of top sheet 3, bottom sheet 4, and first breakable wall 5A, which is a section of breakable sheet 5. The second compartment 12 is formed by a perimeter including top sheet 3, bottom sheet 4 and second breakable wall 5B, which is a second section of breakable sheet 5. The third compartment 13 is formed by a perimeter consisting of bottom sheet 4, breakable wall 5A, seal 7, and breakable wall 5B.

For application as a hot or cold chemical pack, it is intended that the first compartment 11 hold the first substance and the second compartment 12 hold the second substance which, upon intermixing, causes the desired endothermic or exothermic reaction.

For an endothermic reaction, it is known in the art that a reaction of water and ammonium nitrate causes an endothermic reaction and provides for a cold chemical pack. Here, water would be held in one compartment, for illustrative purposes the first compartment 11, and spherically shaped beads (not shown) of ammonium nitrate, a solid salt, known in the art as "prills," would be located in a second compartment, for illustrative purposes the second compartment 12. When a user desires to activate the chemical pack 20 to achieve the desired cold pack, the user would exert a force, such as by squeezing, first compartment 11. This force, hydraulically transmitted by the liquid water in compartment 11, presses against the first breakable wall 5A and causes it to rupture. The same force then is transferred to breakable wall 5B where it ruptures breakable wall 5B. After both breakable walls 5A and 5B are ruptured, the water intermixes with the ammonium nitrate prills causing an endothermic reaction, providing the desired cold pack.

It has been found that due to the forces exerted upon a chemical pack 20 of the FIGS. 1 and 2 embodiment that the first breakable wall 5A ruptures at line 14 and the second breakable wall 5B ruptures at line 15.

It is known in the hot chemical pack art that the crystallization of super-cooled sodium acetate liquid releases heat which is suitable for a hot chemical pack application. It is known that super-cooled sodium acetate liquid is stable, but upon "initiation", begins to crystallize and releases heat. One such way of initiating this crystallization is the intermixing of the super-cooled sodium acetate liquid with sodium acetate crystals (solid). Thus, in use as a hot pack, the super-cooled sodium acetate liquid would be held in a first compartment, e.g., compartment 11, and sodium acetate crystals would be contained in a second compartment, e.g., compartment 12.

It is also known in the hot chemical pack art that the combination of sodium thiosulfate, a solid salt, and glycerine produces an exothermic reaction.

In the applications noted above, the chemical pack 20 would include both a liquid and a solid. In this situation, it is preferable to exert a force upon the compartment containing the liquid, here compartment 11. This force is hydraulically transmitted to the first breakable wall 5A where, when a sufficient force is exerted, ruptures the first breakable wall 5A. The liquid and hydraulic force proceeds to the second breakable wall 5B, where, when a sufficient force is exerted, ruptures wall 5B, causing an intermixing of the liquid and the solid. It is generally not preferred that a force be exerted to a compartment containing a solid, as a solid will not hydraulically transmit the force to the breakable wall 5A, 5B. However, if the compartment containing the solid also contains air or another gas, this gas can be used to hydraulically transmit a force and rupture a breakable wall 5A, 5B.

There are many known endothermic and exothermic reactions which utilize two liquids. In this situation, force could be applied to either compartment 11 or 12 to rupture the breakable walls 5A, 5B.

It is known that a gas or liquid substance migrates across a single plastic sheet at a rate dependent upon the type of plastic and the thickness of the sheet. Prior art devices have attempted to minimize this migration by providing thicker plastic sheets. However, thicker plastic sheets are harder to intentionally rupture to activate the pack.

Since significant migration occurs over time across a single plastic sheet, any design which allows two reactive substances to be placed in proximity should be avoided, or the material of the sheet should be of a thicker, less permeable material.

As mentioned above, the prior art devices suffer from two main shortcomings. First, where a single plastic sheet separates the two reactants, migration of one of the reactants across this sheet causes a pre-activation intermixing of the two reactants which slowly over time causes a significant portion of the reactants to be reacted prior to the desired activation of the device, resulting in a short shelf life and low efficiency upon activation. The present invention overcomes this shortcoming by providing two breakable walls 5A, 5B, and a third compartment 13 interposed between the two compartments 11 and 12 containing the substances to be mixed to provide the endothermic or exothermic reaction.

With the present invention, if a substance migrates through a wall towards the second substance, this substance will enter the third compartment 13. Since migration across a permeable membrane is directly related to the difference in concentration across that permeable membrane, there must first be a significant buildup or concentration of the substance in compartment 13 before it will migrate through the second breakable wall 5B into the second compartment 12. This significantly increases shelf life and reaction efficiency upon activation over the prior art devices.

Second, with the side-by-side multi-compartment bags of the prior art which utilized rupturable seals, it is very difficult to provide a seal which would rupture upon a desired predetermined force. The breakable walls 5A, 5B of the present invention are a much more reliable way of providing a rupturable barrier to provide intermixing of the two substances. The thickness of breakable sheet 5 can be adjusted so that breakable walls 5A and 5B would rupture upon a desired predetermined force.

Figure 11:
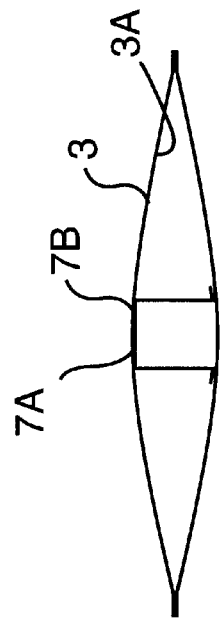
FIGS. 11–18 show side views of alternate embodiments of multi-compartment bags.

The method of manufacturing the multi-compartment bags 20 of the FIGS. 1 and 2 embodiment is shown in FIGS. 6–10. While this manufacturing technique is particularly applicable to the FIGS. 1 and 2 embodiment, it is also applicable to the alternate embodiments (FIGS. 11–18), discussed below, and the multi-use chemical packs (FIGS. 3 and 3A), discussed below. Also, while this method of manufacturing is particularly applicable for multi-compartment bags which have two breakable walls and a third compartment separating the two substances to be mixed, this manufacturing technique may also be used for a multi-compartment bag with just one breakable wall between the two compartments which may be used in situations where the substances do not migrate or have a low migration rate across the breakable wall. FIGS. 11 and 16 represent multi-compartment bags having one breakable wall 5 which separates the two substances to be mixed and which are manufactured by the method of the present invention.

In the discussion as follows, sheets 3, 4 and 5 are generally on rolls which may be the width of a single finished bag or several finished bags. Preferably, sheets 3, 4 and 5 are initially on a roll with a length much longer than an individual bag to provide for continuous manufacturing.

FIGS. 6A and 6B shows the starting point of the manufacturing technique, i.e., providing a first sheet (here sheet 3) for a first exterior wall of the first compartment 11 and the second compartment 12. Sheet 3 has an interior surface 3A to which the breakable sheet (sheet 5) is sealed (seal 7). Preferably, the seals are heat seals which may be made by heat rollers (continuous operation) or by heat bars (stop and start operation) as is known to those of skill in the art. As shown in FIGS. 7A and 7B, preferably, sheet 5 is sealed to sheet 3 along a center section of sheet 5, such that sheet 5 has two loose sides which may be sealed to sheet 4 as discussed below. However, for the embodiment where only one breakable wall is provided (FIG. 11), sheet 5 is sealed to interior surface 3A at a side of sheet 5.

FIGS. 8A and 8B show the loose sides of sheet 5 being sealed to sheet 4 along its interior surface 4A, forming seals 6 and 8.

As shown in FIGS. 9A and 9B, at a lower section, the sides of sheets 3 and 4 are brought together and sealed together via seals 1 and 2. Preferably, seals 1 and 2 are greater than about one bag length but less than about 3 bag lengths so as to facilitate the addition of the first substance 63 and the second substance 64 as discussed below. Also, seal 10 is made so as to form the first compartment 11 and the second compartment 12, both with open ends. Preferably, this and the previous step also form the third compartment 13, also having an open end.

To the open-ended compartments, via hoses or other conduits 61 and 62, the first substance 63 and second substance 64 are added to the open ended first compartment 11 and second compartment 12. If desired, an inert substance may be added to the third compartment 13 at this stage, otherwise the third compartment is left essentially empty or may contain some air. The open end, preferably the top of the open-ended compartments 11, 12, 13 is sealed with a double width seal which forms seal 9 of a bag being completed and seal 10 of a bag prior to its being filled with the first and second substances 63 and 64. Then, the double width seal is cut, forming the completed multi-compartment bag 20.

With this method of manufacturing, seals 9 and 10 are made after and superimposed upon seals 6, 7, and 8. This is the preferred method of manufacturing as this provides a stronger seal about the perimeter of the bag 20 to prevent external leaking while also ensuring that seals 6, 7 and 8 extend the whole width of an individual bag 20 such that there is no internal leaking from one compartment to another.

This method of manufacturing multi-compartment bags 20 may also be used to manufacture the multi-use-packs 30, discussed below, with additional steps apparent to one of skill in the art in light of the disclosure above.

FIGS. 11–18 show alternate embodiments of the multi-compartment bag 20 which may be manufactured by this method.

FIG. 11 shows a single breakable wall embodiment which may be used when the substances do not migrate across the breakable wall 5, there is a slow rate of migration, or the product does not need a long shelf life.

Figure 12:
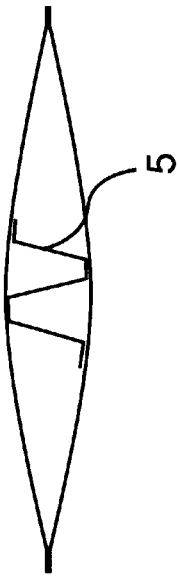

FIG. 12 shows an embodiment similar to the FIGS. 1 and 2 embodiment; however, a single seal 6A is used to seal both breakable walls 5A, 5B to the interior surface 4A of sheet 4.

Figure 13:
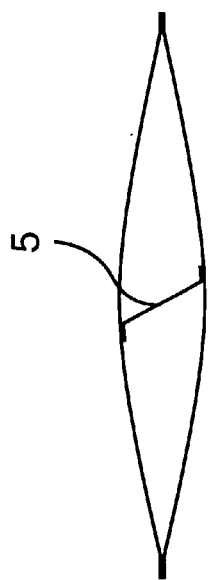

FIG. 13 shows an embodiment where two seals 7A, 7B are used in place of seal 7 to seal sheet 5 to the interior surface 3A of sheet 3.

Figure 14:
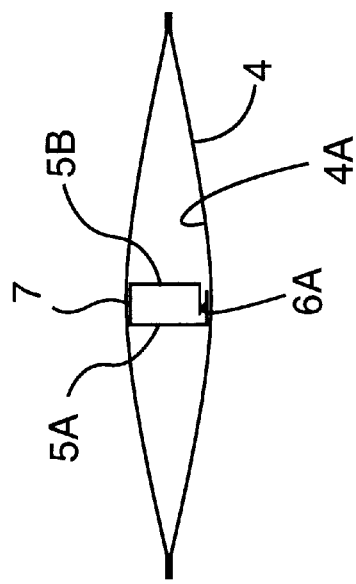

FIG. 14 shows an embodiment where three breakable walls and two compartments are utilized to separate the compartments holding the first and second substances. This may be used to provide additional shelf life or to further reduce the number of chemical packs which are unintentionally activated during shipping and handling.

Figure 17:
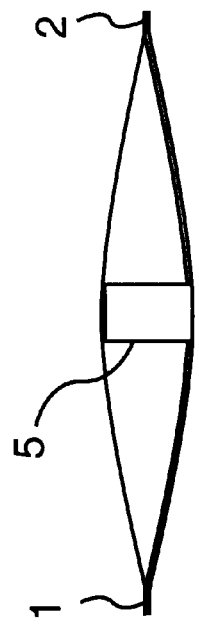
Figure 18:
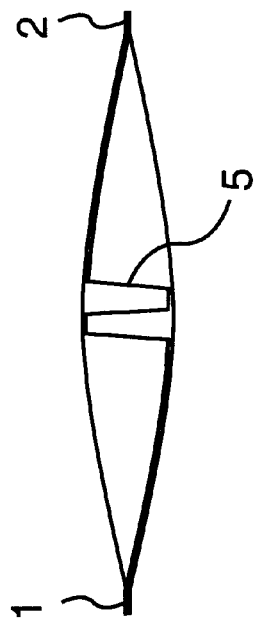
Figure 15:
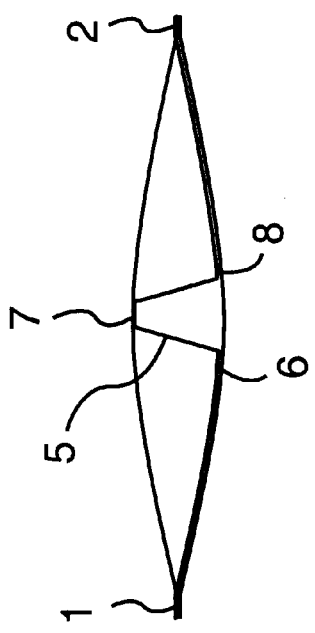
Figure 16:
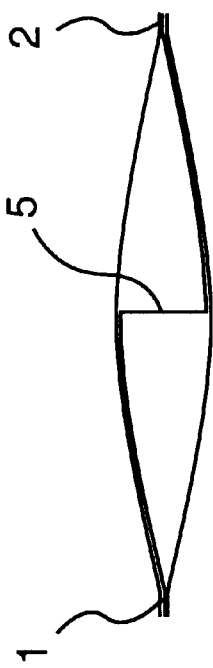

FIG. 15 shows an embodiment similar to FIGS. 1 and 2 where sheet 5 is wider and extends to seals 1 and 2. Under some circumstances, this and the other embodiments, below, which utilize a wider sheet 5 may be easier to manufacture. However, the method and the product which utilize the smaller width sheet 5 are generally preferred as there is a materials savings with a shorter width sheet 5. FIGS. 16, 17, and 18 are similar to FIGS. 11, 13, and 14, respectively, except that sheet 5 extends to seals 1 and 2.

Figure 3:
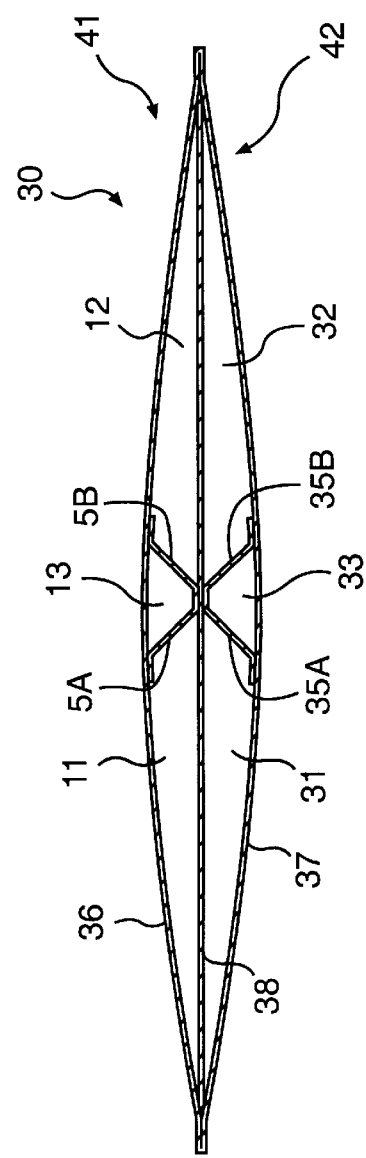
FIGS. 3 and 3A are side views of multi-use chemical packs which provide for two uses.
Figure 3A:
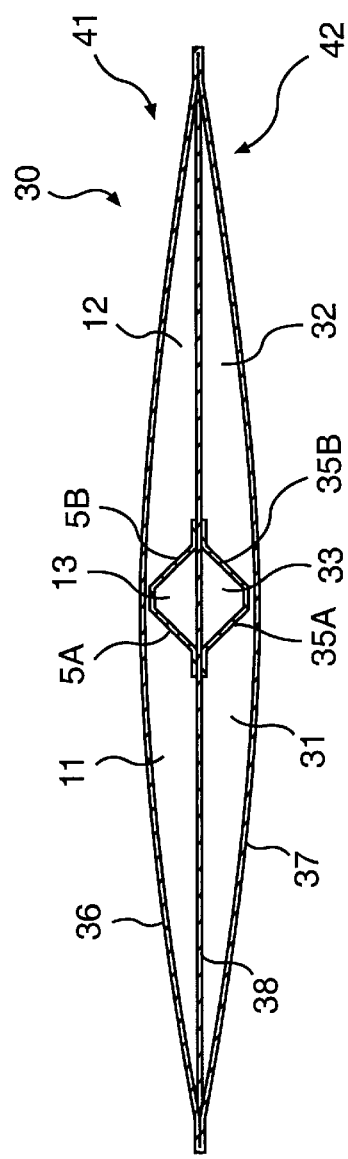

FIGS. 3 and 3A show alternate embodiments of the present invention, a multi-use hot or cold chemical pack 30. Generally, the FIG. 3 embodiment is preferred as it is believed easier to manufacture. Similar to the FIGS. 1 and 2 embodiment, this multi-use pack 30 includes a "first-use" pack 41 which includes a first compartment 11, a second compartment 12, a third compartment 13, a first breakable wall 5A and second breakable wall 5B, where the breakable walls 5A, 5B and compartment 13 separate the first compartment 11 and the second compartment 12. A "second-use" pack 42, represented by fourth compartment 31, fifth compartment 32, sixth compartment 33, third breakable wall 35A, and fourth breakable wall 35B operates in a similar fashion as discussed above.

For multi-use chemical packs 30 which use a liquid substance to be combined with a solid substance, it is preferred that the second-use pack 42 be a reverse mirror image of the first use pack 41. Thus, if the liquid substance is contained in compartment 11 of the first-use pack 41, then the liquid substance would be contained in fifth compartment 32 of the second-use pack 42, such that a compartment containing a liquid is in proximity with a compartment containing a solid substance on each side of the multi-use pack 30. This reverse mirror image orientation is preferred as liquids transfer hydraulic force and solids do not. This is preferred because, if the first-use pack 41 is desired to be activated, the user applies a force, e.g., by squeezing, the liquid containing compartment to force the liquid to rupture the breakable walls. Since the solid material on the same side of the multi-use pack 30 which is receiving the same force does not transfer the force, only the first-use pack 41 activates and the second-use pack 42 does not activate until a force is applied to its liquid containing compartment.

An important advantage of the multi-use pack 30 is that it can be used more than once, which makes the pack more convenient to use and less costly for the user. Also, one multi-use pack 30 could be used both as a hot and cold pack, which increases the versatility of the pack while reducing its cost to the user.

With the embodiment of FIG. 3, it is preferred that sheet 38 be of a thicker or a more impermeable plastic to prevent the migration of a substance across sheet 38 into the substance on the other side of sheet 38, such that the multi-use pack 30 maintains a long shelf life and high efficiency upon activation. Sheet 38 may also be made from a material that has hot or cold insulating properties, such as, for example, a layer of foam material. Sheet 38 may be constructed of an insulating material when it is desired that the heat or cold generated by multi-use pack 30 be directed substantially toward the exterior surface 36 for the first-use pack 41 and exterior surface 37 for the second-use pack 42, so as to increase efficiency upon use.

Figures 4, 5:
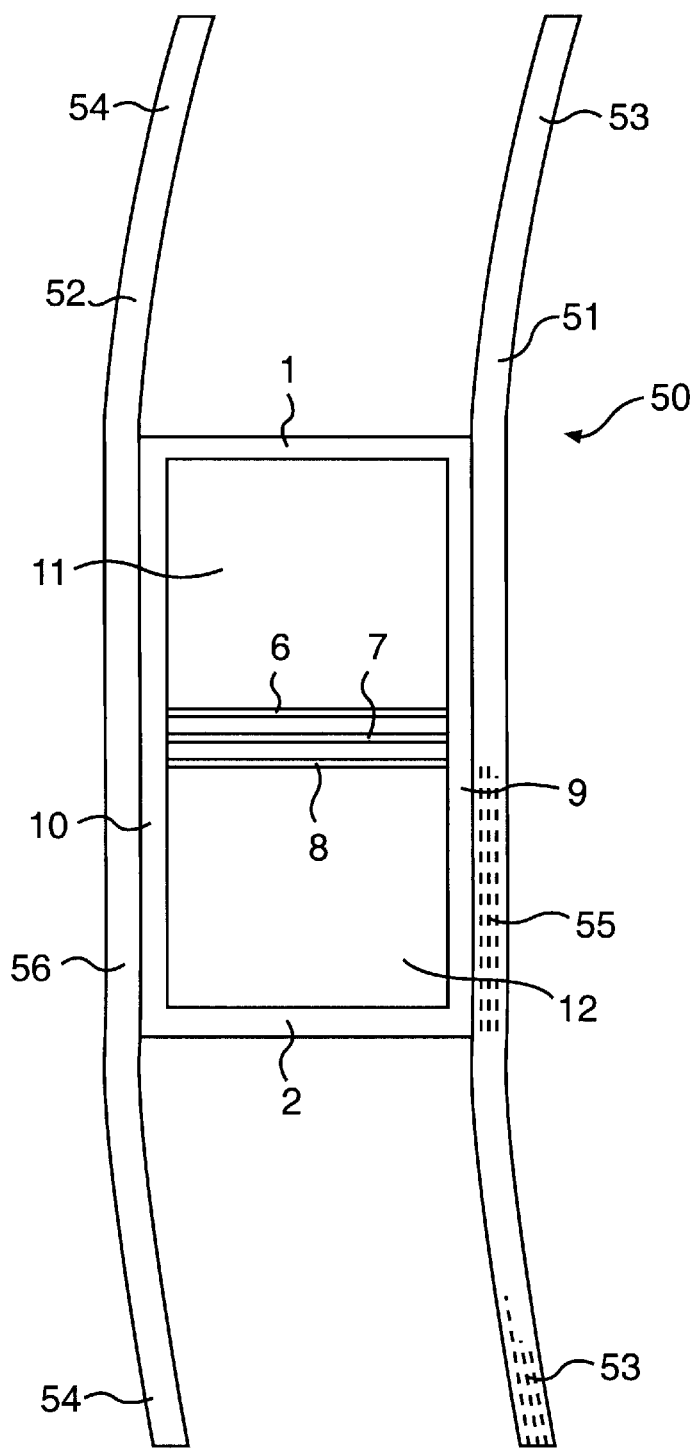
FIG. 4 is a top view of a multi-compartment bag having ties.
FIG. 5 is an end view of the multi-compartment bag of FIG. 4.
Figure 10:
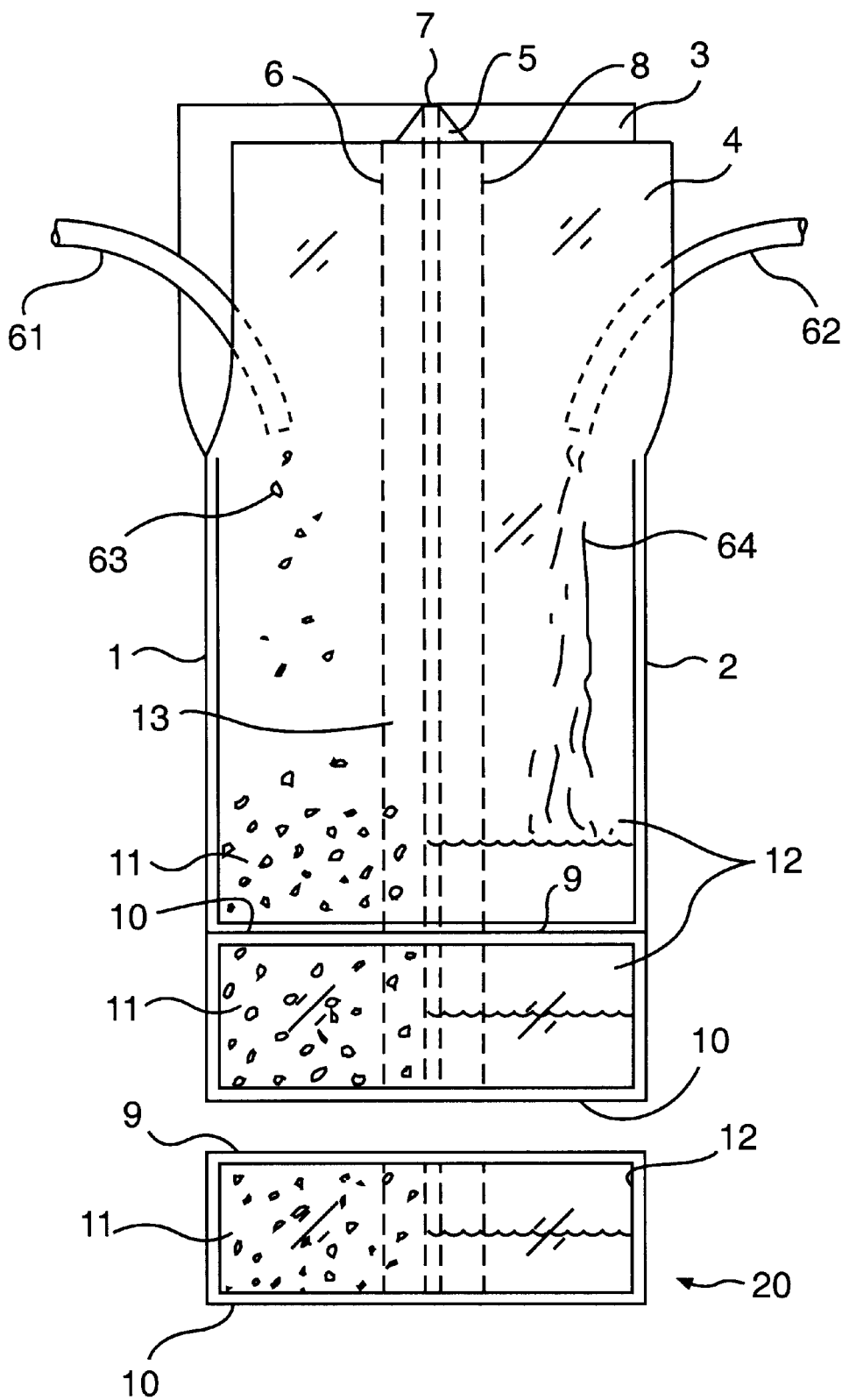

FIGS. 4 and 5 show an alternate embodiment of the FIGS. 1 and 2 device (like numerals used for corresponding parts) which includes a first elongated strip 51 and a second elongated strip 52 which together serve as ties such that a user may fasten a multi-compartment bag or a multi-use chemical pack to a particular part of his body. The first and second elongated strips 51, 52 may be fastened to the bag 50 in any suitable way. Preferably, strips 51, 52 are sealed to perimeter seals, i.e., seals 1, 2, 9, and 10. While strips 51, 52 are shown sealed to seals 9 and 10, alternatively, the strips 51 and 52 could be sealed to seals 1 and 2. Most preferably, the strips 51 and 52 are folded over two perimeter seals, shown here as seals 9 and 10, then sealed to the existing seal, such that at the portion of the strip 51, 52 which is sealed to the bag 50, there exist four layers of materials, i.e., sheets 3 and 4 and two folded sections of the strips 51, 52. If folded, it is preferred that the strips 51, 52 be folded along their entire length, as this provides a stronger tie.

Thus, it can be seen that the first elongated strip 51 has a center section 55 which is sealed to seal 9 and two ends 53 which extend longitudinally from seal 9. Likewise, the second elongated strip 52 has a center section 56 which is sealed to seal 10 and has two ends 54 which extend longitudinally from seal 10.

This method of attaching strips 51, 52 as ties is preferred as it does not cause stresses which would tend to tear the bag 50 and release chemicals upon the user. The strips 51, 52 are preferably installed after the bag 50 has been assembled, including filled with the desired substances. As such, care should be taken such that when the strips 51 and 52 are fastened or sealed to the bag 50 they do not extend into the first compartment 11 or second compartment 12 so as to weaken these compartments or cause exterior leaking of the chemical.

For hot or cold packs where it is desired to mix two substances to achieve the endothermic or exothermic reaction, the third compartment 13 may be essentially empty or it may contain an inert substance such as air or inert gas which may allow the breakable walls 5A, 5B to break easier due to the compressive nature of the gas. In liquid/liquid systems, having some air or inert gas may be advantageous because, in a situation such as a bag-in-bag design where liquid is on both sides of the wall to be ruptured, it can be difficult to rupture the wall. Also, in liquid/liquid systems, a certain amount of gas, such as air or nitrogen is helpful in allowing for the quick mixing of the two liquids.

Figure 1A:
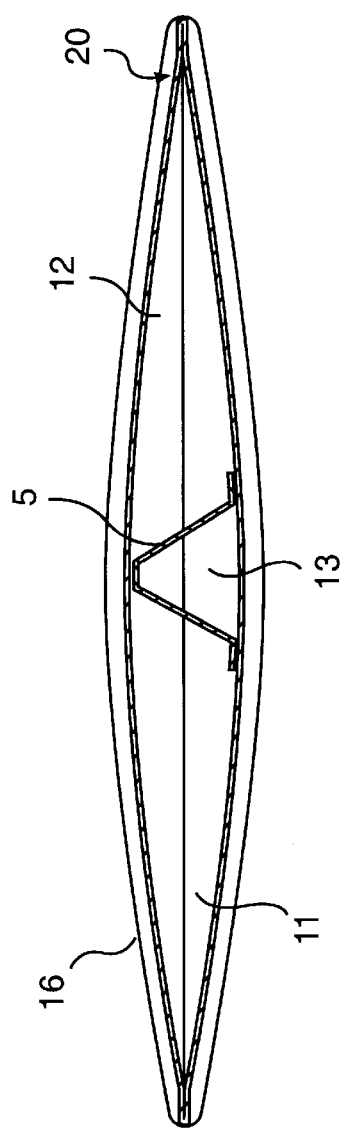

The bags 20 and multi-use packs 30 may be used without a cover or may include a non-woven soft exterior cover 16 (FIG. 1A) which substantially surrounds the bag, such as paper or other materials to increase the user's comfort.

The bags 20 and multi-use packs 30 of the present invention, may be formed in any size or shape to meet their intended purpose or fit an intended body area and it is not intended that the figures shown herein are limiting in any way as to the shapes which are covered by this patent. For each design, the two substances which are to be mixed should be separated by two walls, at least a portion of which are breakable walls, and a third compartment which may be substantially empty or contain air or an inert substance.

Sheets 3, 4, and 5 may be of any suitable material. Preferably sheets 3, 4, and 5 are of a relatively flexible, plastic or vinyl sheet material, e.g., polyethylene, polypropylene, polyvinylchloride, mylar, cellophane or vinyl. Generally, any flexible sheet material may be used as long as it is capable of being effectively sealed as discussed herein. Generally, breakable sheet 5, if made of the same plastic as sheets 3 and 4, is thinner than sheets 3 and 4 such that breakable sheet 5 would rupture before sheets 3 and 4. Breakable sheet 5 may alternatively be made of a different, weaker plastic than sheets 3 and 4 such that breakable sheet 5 will rupture before sheets 3 and 4.

Seals 1, 2, 6, 7, 8, 9, and 10 are preferably strong heat seals. However, any suitable method of sealing these sheets at the desired location may be used, such as, for example, an RF seal, ultrasonic seals, glue, etc.

The multi-compartment bags 20 and multi-use packs 30 may be manufactured in a variety of configurations. For example, breakable sheet 5 could be substituted for by two separate sheets, each sheet forming a breakable wall. Also, the breakable walls 5A, 5B could be just a portion of a larger wall.

The multi-compartment bags 20 and the multi-use packs 30 solve the problems mentioned above by providing a chemical pack which has a long shelf life, high efficiency upon activation, high reliability, and ease of use. These advantages are due to the inventive concept of providing a third compartment 13 between the two compartments 11 and 12 containing the two substances to be mixed. The third compartment 13 is essentially empty or contains an inert substance and its perimeter includes two breakable walls 5A, 5B which allow intermixing of the two substances.

Although the present inventions and its advantages have been described in detail, it should be understood that various changes, substitutions, and alterations can be made therein without departing from the spirit and scope of the invention as defined by the appended claims.

What is claimed is:

1. A multi-use hot or cold chemical pack, comprising:
   a first compartment for holding a first substance having a first breakable wall;
   a second compartment for holding a second substance having a second breakable wall;
   a third compartment interposed between the first compartment and the second compartment having a perimeter including the first breakable wall and the second breakable wall;
   a fourth compartment for holding a third substance having a third breakable wall;
   a fifth compartment for holding a fourth substance having a fourth breakable wall; and
   a sixth compartment interposed between the fourth compartment and the fifth compartment having a perimeter including the third breakable wall and the fourth breakable wall;
   wherein the first compartment is proximal to the fourth compartment and the second compartment is proximal to the fifth compartment.

2. The multi-use pack of claim 1, wherein when a first sufficient force is exerted upon the pack, the first breakable wall and the second breakable wall rupture, causing mixing of the first substance and the second substance.

3. The multi-use pack of claim 2, wherein when a second sufficient force is exerted upon the pack, the third breakable wall and the fourth breakable wall rupture, causing mixing of the third substance and the fourth substance.

4. The multi-use pack of claim 1 wherein the third compartment acts as a barrier between the first compartment and the second compartment to minimize pre-activation intermixing of the first substance and the second substance.

5. The multi-use pack of claim 1, wherein the sixth compartment acts as a barrier between the fourth compartment and the fifth compartment to minimize pre-activation intermixing of the third substance and the fourth substance.

6. The multi-use pack of claim 1, wherein the second and third substances comprise a solid substance.

7. The multi-use pack of claim 6, wherein the second and third substances comprise a plurality of prills.

8. The multi-use pack of claim 1, further comprising two strips fastened to the pack to serve as ties.

9. A multi-use hot or cold chemical pack, comprising:
   a first sheet, a second sheet and a third sheet, wherein the first sheet, the second sheet and the third sheet are sealed together to form a first internal compartment and a second internal compartment;
   a first breakable wall, a second breakable wall, a third breakable wall and a fourth breakable wall;
   wherein the first breakable wall and the second breakable wall are arranged in the first internal compartment and are sealed to the first sheet and the second sheet so as to form a first compartment for holding a first substance, a second compartment for holding a second substance, and a third compartment interposed between the first and the second compartment;
   wherein the third breakable wall and the fourth breakable wall are arranged in the second internal compartment and are sealed to the second sheet and the third sheet so as to form a fourth compartment for holding a third substance, a fifth compartment for holding a fourth substance, and a sixth compartment interposed between the fourth compartment and the fifth compartment;
   wherein the first compartment is proximal to the fourth compartment and the second compartment is proximal to the fifth compartment.

10. The multi-use pack of claim 9, wherein when a first sufficient force is exerted upon the pack, the first breakable wall and the second breakable wall rupture, causing mixing of the first substance and the second substance.

11. The multi-use pack of claim 10, wherein when a second sufficient force is exerted upon the pack, the third breakable wall and the fourth breakable wall rupture, causing mixing of the third substance and the fourth substance.

12. The multi-use pack of claim 9, wherein the third compartment acts as a barrier between the first compartment and the second compartment to minimize pre-activation intermixing of the first substance and the second substance.

13. The multi-use pack of claim 9, wherein the sixth compartment acts as a barrier between the fourth compartment and the fifth compartment to minimize pre-activation intermixing of the third substance and the fourth substance.

14. The multi-use pack of claim 9, wherein the second and third substances comprise a solid substance.

15. The multi-use pack of claim 14, wherein the second and third substances comprise a plurality of prills.

16. The multi-use pack of claim 9, further comprising two strips fastened to the pack to serve as ties.

* * * * *